United States Patent [19]
Berthe

[11] Patent Number: 5,276,225
[45] Date of Patent: Jan. 4, 1994

[54] PROCESS FOR SEPARATING HYDROGEN FLUORIDE FROM ITS MIXTURES WITH 1,1,1-TRIFLUORO-2-CHLOROETHANE

[75] Inventor: Bernard Berthe, Marseille, France
[73] Assignee: Elf Atochem S.A., France
[21] Appl. No.: 43,136
[22] Filed: Mar. 31, 1993

Related U.S. Application Data

[63] Continuation of Ser. No. 867,659, Apr. 13, 1992, abandoned.

[30] Foreign Application Priority Data

Apr. 17, 1991 [FR] France ................. 91 04736

[51] Int. Cl.⁵ ............................... C07C 17/38
[52] U.S. Cl. ........................ 570/178; 570/177
[58] Field of Search .................... 570/177, 178

[56] References Cited

U.S. PATENT DOCUMENTS

| | | | |
|---|---|---|---|
| 4,129,603 | 8/1978 | Bell | 570/177 |
| 4,209,470 | 6/1980 | Lorquet | 570/178 |
| 4,911,792 | 3/1990 | Manzer et al. | 570/178 |
| 4,944,846 | 7/1990 | Manzer et al. | 570/178 |
| 5,094,773 | 3/1992 | Manzer et al. | 570/178 |

FOREIGN PATENT DOCUMENTS

| | | | |
|---|---|---|---|
| 0003147 | 7/1979 | European Pat. Off. | 570/178 |
| 098341 | 1/1984 | European Pat. Off. | 570/177 |
| 353970 | 2/1990 | European Pat. Off. | 570/178 |
| 354697 | 2/1990 | European Pat. Off. | 570/178 |
| 0462514A1 | 12/1991 | European Pat. Off. | |
| 0509449A2 | 10/1992 | European Pat. Off. | |
| WO91/04955 | 4/1991 | PCT Int'l Appl. | |

Primary Examiner—Werren B. Lone
Attorney, Agent, or Firm—Morgan & Finnegan

[57] ABSTRACT

A halocarbon product made from the reaction of excess hydrogen fluoride with a halocarbon, containing excess hydrogen fluoride as an azeotrope is purified by fluorination in the presence of additional halocarbon or haloolefin.

5 Claims, 1 Drawing Sheet

PROCESS FOR SEPARATING HYDROGEN FLUORIDE FROM ITS MIXTURES WITH 1,1,1-TRIFLUORO-2-CHLOROETHANE

This is a continuation of co-pending application Ser. No. 07/867,659, filed on Apr. 13, 1992, abandoned.

FIELD OF THE INVENTION

The invention relates to the separation of hydrogen fluoride (HF) from its mixtures with 1,1,1-trifluoro-2-chloroethane (F133a), which is an important synthesis intermediate capable of being employed especially for the manufacture of 1,1,1,2-tetrafluoroethane (F134a).

BACKGROUND OF THE INVENTION

The process according to the invention applies more particularly to the separation of the unconverted HF present in mixtures originating from the manufacture of F133a by fluorination of trichloroethylene or of symmetrical or unsymmetrical tetrachloroethane. For economic reasons, HF must be recovered in anhydrous form to allow it to be recycled to the fluorination reactor.

Various techniques for performing this separation of HF and chlorofluorohydrocarbons have already been described. There may be mentioned, for example:

U.S. Pat. No. 2,640,086, which relates to the separation of HF and of chlorodifluoromethane and employs chloroform to promote the separation into two phases, an HF-rich phase and an HF-poor phase;

U.S. Pat. No. 3,873,629, relating to a continuous process for the separation of HF and of chlorodifluoromethane and consisting in bringing the gaseous mixture of the two constituents into counter-currentwise contact with sulphuric acid;

U.S. Pat. No. 3,976,447, which proposes a separation of HF from gaseous effluents by absorption-desorption on calcium, barium or strontium chloride particles;

U.S. Pat. No. 4,209,470, which describes a process for separating HF from its mixtures with 1-chloro-1,1-difluoroethane, in which, to improve the phase separation, an auxiliary liquid is added, consisting wholly or predominantly of 1,1-dichloro-1-fluoroethane;

patent application No. EP 0,353,970, relating to the separation of HF from its mixtures with 2,2-dichloro-1,1,1-trifluoroethane and/or 2-chloro-1,1,1,2-tetrafluoroethane by phase separation and distillation.

In the case of mixtures of HF and F133a, a simple distillation does not enable them to be separated because HF and F133a form an azeotrope which is more volatile than HF or F133a; the HF content of this azeotrope is approximately 60 mol % (20% by weight). There are no data in the literature on the phase separation of mixtures of HF and F133a; at room temperature and whatever the HF and F133a concentrations, mixtures of HF and F133a do not separate into two phases.

DETAILED DESCRIPTION OF THE INVENTION

It has now been found that it is possible to obtain an excellent separation of a mixture of HF and F133a, provided that it is cooled to a temperature below 0° C., preferably of between −40° C. and −10° C. Thus, for example at −20° C., the phase separation of the HF-F133a azeotrope mixture yields an organic lower phase which contains only 2.7% by weight of HF (14 mol %) and an acidic upper phase containing 60% by weight of HF (90 mol %). Consequently, by combining phase separation and distillation it has been found possible to obtain, if need be, a complete separation of HF and of F133a.

The process for separating HF and F133a according to the invention is therefore characterized in that:

a) the mixture of HF and F133a is subjected to a phase separation at a temperature below −0° C., b) the HF-poor organic lower phase thus obtained is distilled so as to separate off at the head the HF present in this phase, in the form of HF-F133a azeotrope which is returned to the phase separator, and to recover the excess F133a at the foot, and c) the HF-rich upper phase is either recycled directly to the fluorination reactor or is subjected to a distillation so as to separate at the head the F133a present in this phase, in the form of HF-F133a azeotrope which is returned to the phase separator, and to recover practically pure HF at the foot.

BRIEF DESCRIPTION OF THE DRAWINGS

The operation of the process according to the invention will be understood better by referring to the diagrams shown in FIGS. 1 and 2. The diagrams are not considered limiting.

Figure 1:
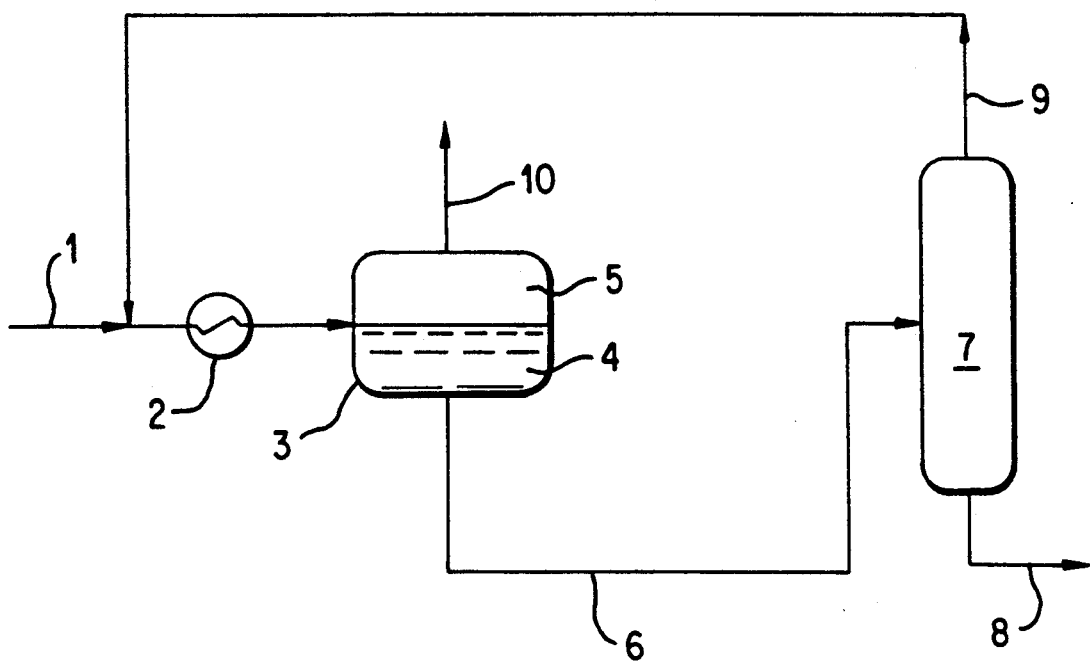
FIG. 1 and FIG. 2 schematically depict the process of the present invention.

The mixture to be separated, consisting essentially of HF and F133a, cooled beforehand by means of an exchanger 2, is fed by the conduit 1 into the phase separator 3 maintained at a temperature below 0° C., preferably between −40° C. and −10° C. When demixing takes place, an HF-poor organic lower phase 4 and an HF-rich upper phase 5 are then obtained in the phase separator. The organic phase 4 originating from the phase separator 3 feeds via 6 a distillation column 7, at the top of which an effluent 9 composed of the HF and F133a azeotrope is taken off; this effluent 9 is returned to the phase separator 3 upstream of the exchanger 2 for separation into two phases. At the foot of the column 7 a stream 8 of pure F133a is recovered.

The HF-rich upper phase 5 leaving by the conduit 10 can be recycled as it is directed to the fluorination reactor for the production of F133a (FIG. 1). However, according to FIG. 2, corresponding to the preferred embodiment of the process according to the invention, the HF-rich upper phase 5 is delivered by the conduit 10 to a distillation column 11, at the head of which an effluent 13 composed of the HF and F133a azeotrope is taken off, and this, like the effluent 9, is returned to the phase separator 3 upstream of the exchanger 2 for separation into two phases. At the foot of the column 11 practically pure HF is then recovered at 12.

The transfer from the phase separator to the distillation columns and from the latter towards the phase separator takes place through the intermediacy of expansion valves or pumps, depending on the operating pressures of the phase separator and of the distillation columns. The temperature of the streams feeding the distillation columns via 6 and 10 can be adjusted by means of exchangers to obtain an optimum distillation.

Figure 2:
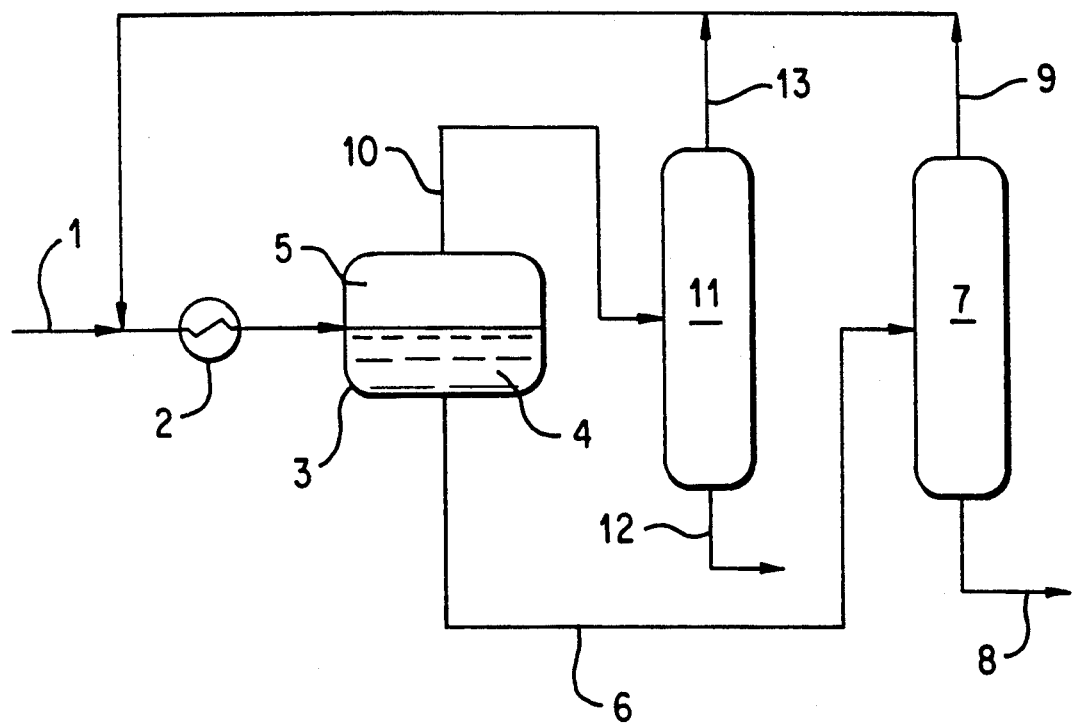

By way of example, the following table gives the molar compositions, temperatures and pressures of the various streams obtained when proceeding in accordance with the diagram of FIG. 2, starting with a mixture (1) of HF and F133a containing from 14 to 90 mol% of HF and from 10 to 86 mol% of F133a.

TABLE I

|  | Organic phase (4) | HF phase (5) | Head of the columns (9 and 13) | Foot of column 7 (8) | Foot of column 11 (12) |
|---|---|---|---|---|---|
| HF (mol %) | 14 | 90 | 60 | — | 100 |
| F133a (mol %) | 86 | 10 | 40 | 100 | — |
| Temperature (°C.) | −20 | −20 | +17 | +27 | +43 |
| Pressure (bars absolute) | 15 | 15 | 2.2 | 2.2 | 2.2 |

Tests at different pressures (1, 10, 15 and 25 bars) have shown that this parameter has no appreciable influence on the phase separation of the mixture of HF and F133a. Its influence on the temperatures at the foot and at the head of columns 7 and 11 is illustrated in the following Tables II and III:

TABLE II

|  | Organic phase (4) | HF phase (5) | Head of the columns (9 and 13) | Foot of column 7 (8) | Foot of column 11 (12) |
|---|---|---|---|---|---|
| HF (mol %) | 14 | 90 | 60 | — | 100 |
| F133a (mol %) | 86 | 10 | 40 | 100 | — |
| Temperature (°C.) | −20 | −20 | +42 | +54 | +70 |
| Pressure (bars absolute) | 15 | 15 | 5 | 5 | 5 |

TABLE III

|  | Organic phase (4) | HF phase (5) | Head of the columns (9 and 13) | Foot of column 7 (8) | Foot of column 11 (12) |
|---|---|---|---|---|---|
| HF (mol %) | 14 | 90 | 60 | — | 100 |
| F133a (mol %) | 86 | 10 | 40 | 100 | — |
| Temperature (°C.) | −20 | −20 | +66 | +81 | +96 |
| Pressure (bars absolute) | 15 | 15 | 10 | 10 | 10 |

The temperature is the essential parameter for the phase separation. In fact, above 15° C. no phase separation is observed, whatever the composition of the HF-F133a mixture. At −20° C. the separated HF phase contains 60% by weight of HF; this content goes down to 50% at a phase separation temperature of −5° C. At this latter temperature the separated organic phase contains 5% by weight of HF; this content drops to 2.7% when the phase separation is performed at −20° C. Good control of the temperature in the phase separator is therefore important for obtaining an optimum phase separation.

In the mixture of HF and F133a fed to the phase separator, the HF content can range from 14 to 90 mol %; in most cases it is between 25 and 75%.

When F133a is prepared by fluorination of trichloroethylene or of a tetrachloroethane, the effluents from the fluorination reactor generally contain, in addition to F133a and to unconverted HF, hydrochloric acid, which can be easily removed by distillation, and a small proportion (up to 20% by weight relative to F133a) of other organic compounds such as, for example, trichloroethylene, monofluorotrichloroethane and difluorodichloroethane. Phase separation tests have shown that the presence of these organic compounds is in no case detrimental to the phase separation and can even promote it. By way of example, Table IV below shows the molar streams obtained by proceeding in accordance with the diagram of FIG. 2, starting with the effluent from a reactor for the fluorination of trichloroethylene to F133a. This effluent, which contains a little 1,1-difluoro-1,2-dichloroethane (F132b), is predistilled to remove the byproduct hydrochloric acid and feeds the phase separator 3 via the conduit 1. This effluent is cooled to −20° C. by the exchanger 2 and the phase separator is maintained at −20° C.

TABLE IV

|  | FLOWS IN MOLES/HOUR: | | |
|---|---|---|---|
|  | HF | F133a | F132b |
| Feed (1) | 40 | 19 | 1 |
| Organic phase (4) | 2.7 | 20.8 | 0.94 |
| HF phase (5) | 45.7 | 3.8 | 0.06 |
| Head of column 11 (13) | 5.7 | 3.8 | — |
| Head of column 7 (9) | 2.7 | 1.8 | — |
| Foot of column 11 (12) | 40 | — | 0.06 |
| Foot of column 7 (8) | — | 19 | 0.94 |

The foot of the column 11, containing chiefly HF and traces of F132b, can be returned as such to the fluorination reactor.

The foot of the column 7, containing F133a and most of the F132b fed to the phase separator, is then distilled to obtain pure F133a at the head of the column. The foot of this distillation column, very rich in F132b, is then returned to the fluorination reactor.

It is found that the molar content of HF of the organic phase (4) thus obtained is only 11%, which should be compared with that (14%) obtained in the absence of F132b.

The separation process according to the invention applies, therefore, not only to HF-F133a binary mixtures but also to the crude fluorination mixtures after removal of the byproduct HCl.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. Process for separating hydrogen fluoride (HF) from its mixtures with 1,1,1-trifluoro-2-chloroethane comprising:
   a) the mixture of HF and 1,1,1-trifluoro-2-chloroethane is subjected to a phase separation at a temperature below −0° C.,
   b) the HF-poor organic lower phase thus obtained is distilled to separate off at the head of a distillation column the HF present in this phase, in the form of a HF-1,1,1-trifluoro-2-chloroethane azeotrope which is returned to a phase separator, and to recover excess 1,1,1-trifluoro-2-chloroethane at the foot of the distillation column, and
   c) the HF-rich upper phase is either recycled directly to a fluorination reactor or is subjected to a distillation to separate at the head of the distillation column the 1,1,1-trifluoro-2-chloroethane present in this phase, in the form of a HF-1,1,1-trifluoro-2-chloroethane azeotrope which is returned to the phase separator, and to recover practically pure HF at the foot.

2. Process according to claim 1, wherein the temperature of phase separation is between −40° C. and −10° C.

3. Process according to claim 1, wherein the HF content of the mixture to be treated is between 14 and 90mol %.

4. Process according to claim 1, wherein the mixture of HF and 1,1,1-trifluoro-2-chloroethane to be treated also contains up to 20% by weight of other organic compounds (% expressed relative to 1,1,1-trifluoro-2-chloroethane).

5. Process according to claim 3, wherein the HF content is between 25 and 75 mol %.

* * * * *